US009562878B2

(12) United States Patent
Graham et al.

(10) Patent No.: US 9,562,878 B2
(45) Date of Patent: Feb. 7, 2017

(54) RAIL CONDITION MONITORING SYSTEM WITH CARRIAGE

(71) Applicant: Nordco Inc., Oak Creek, WI (US)

(72) Inventors: Patrick Michael Graham, Watertown, CT (US); Paulo J. Dos Santos, New Milford, CT (US)

(73) Assignee: NORDCO INC., Oak Creek, WI (US)

( * ) Notice: Subject to any disclaimer, the term of this patent is extended or adjusted under 35 U.S.C. 154(b) by 628 days.

(21) Appl. No.: 14/025,402

(22) Filed: Sep. 12, 2013

(65) Prior Publication Data

US 2014/0069193 A1 Mar. 13, 2014

Related U.S. Application Data

(60) Provisional application No. 61/700,753, filed on Sep. 13, 2012.

(51) Int. Cl.
*G01N 29/04* (2006.01)
*G01N 29/07* (2006.01)
*G01N 29/265* (2006.01)
*G01N 29/44* (2006.01)

(52) U.S. Cl.
CPC .............. *G01N 29/04* (2013.01); *G01N 29/07* (2013.01); *G01N 29/265* (2013.01); *G01N 29/4427* (2013.01); *G01N 2291/2623* (2013.01)

(58) Field of Classification Search
CPC ............ G01N 2291/2623; G01N 29/07; G01N 29/4427; G01N 29/265
USPC ........................................ 73/636, 635, 639
See application file for complete search history.

(56) References Cited

U.S. PATENT DOCUMENTS

| | | | |
|---|---|---|---|
| 5,386,727 A | * | 2/1995 | Searle ................ G01N 29/2493 73/602 |
| 5,837,880 A | | 11/1998 | Shakinovsky et al. |
| 5,970,438 A | | 10/1999 | Clark et al. |
| 6,055,862 A | | 5/2000 | Martens |
| 6,476,603 B2 | * | 11/2002 | Clark ...................... B61K 9/10 324/217 |
| 6,594,591 B2 | | 7/2003 | Clark et al. |
| 6,600,999 B2 | | 7/2003 | Clark et al. |
| 7,849,748 B2 | | 12/2010 | Havira |
| 7,882,742 B1 | | 2/2011 | Martens |
| 8,181,529 B2 | | 5/2012 | Crocker et al. |
| 8,365,604 B2 | | 2/2013 | Kahn |
| 8,418,563 B2 | | 4/2013 | Wigh et al. |
| 8,424,387 B2 | | 4/2013 | Wigh et al. |
| 8,485,035 B2 | | 7/2013 | Wigh et al. |
| 8,739,631 B2 | | 6/2014 | Havira et al. |
| 8,806,948 B2 | | 8/2014 | Kahn et al. |

(Continued)

*Primary Examiner* — Michael A Lyons
*Assistant Examiner* — Suman K Nath
(74) *Attorney, Agent, or Firm* — Greer, Burns & Crain, Ltd.

(57) ABSTRACT

A rail condition monitoring carriage for use on a railroad track is provided, including at least one frame movable along the railroad track, an ultrasonic rail condition monitor disposed on the at least one frame and configured for ultrasonically monitoring condition of the railroad track and transmitting the condition data to a remote location, a gage measurement device disposed on the at least one frame for monitoring a gage value of the track, collecting gage data and transmitting the gage data to the remote location, and a control system connected to the rail condition monitor and the gage measurement device for receiving the collected data and evaluating same.

13 Claims, 13 Drawing Sheets

(56) References Cited

U.S. PATENT DOCUMENTS

| | | |
|---|---|---|
| 8,820,166 B2 | 9/2014 | Wigh et al. |
| 2009/0282923 A1 | 11/2009 | Havira |
| 2009/0320603 A1 | 12/2009 | Crocker et al. |
| 2011/0043199 A1 | 2/2011 | Crocker |
| 2011/0209549 A1 | 9/2011 | Kahn |
| 2012/0218868 A1* | 8/2012 | Kahn .................. G01N 29/265 367/99 |
| 2013/0047729 A1 | 2/2013 | Wigh et al. |
| 2013/0047730 A1 | 2/2013 | Wigh et al. |
| 2013/0152691 A1 | 6/2013 | Wigh et al. |
| 2013/0220019 A1 | 8/2013 | Havira et al. |
| 2013/0220020 A1 | 8/2013 | Wigh et al. |
| 2014/0251015 A1 | 9/2014 | Havira et al. |

\* cited by examiner

RAIL CONDITION MONITORING SYSTEM WITH CARRIAGE

RELATED APPLICATION

The present application claims 35 USC 119 priority from U.S. Provisional Application No. 61/700,753 filed Sep. 13, 2012.

BACKGROUND

The present invention generally relates to rail track inspection equipment, and more specifically to equipment for automatically monitoring the condition of railroad rails.

US railroads are subject to several different track inspection processes. First, as dictated by the Federal Railroad Administration (FRA), the railroads are required to visually inspect the rail on a regular basis. The frequency of these visual inspections is determined by the speed at which the railroad wishes trains to travel on the specific rail in question, also known as the Class or Classification of the track. For Class 4 and 5 track, the railroad is required to traverse the rail (by foot or on a hy-rail vehicle) twice weekly, with at least one calendar day intervals between tests. As is known in the art, a hy-rail vehicle is a standard truck equipped for travel along railroad track, with a set of hydraulically operated rail-type wheels mounted to the front and rear of the vehicle.

In addition to visual track inspections required by the FRA, a frequent, periodic search for internal defects must be conducted for all rails in Classes 4 through 5 tracks. The practice of searching for internal flaws is known as rail flaw detection using Non Destructive Testing techniques such as Ultrasonic Testing.

Current standard practice for rail flaw detection utilizes a process that is referred to as stop/start testing (SST). A custom SST rail flaw detection vehicle outfitted with real time on screen displays travels along the track looking for rail defects. At least one on-board operator interprets the on screen results and determines when to stop and verify that a defect exists. Testing frequency along the track is typically scheduled by the railroad based on predetermined risk management guidelines. The railroads balance the cost of increased test frequency versus the reduction of service failures (an interruption in revenue service) and derailments. In practice, railroad test frequencies typically far exceed the requirements by the FRA. However, for railroads, the cost of purchasing, maintaining and staffing and/or subcontracting conventional customized rail flaw detection vehicles prevents their widespread use, and accordingly limits the coverage and/or frequency of track monitoring.

Another drawback of conventional SST testing is that the typical ultrasonic system installation onto a testing vehicle involves a complex collection of cable wiring, ultrasonic signal cables, water plumbing, pneumatic air lines, and hydraulic hose, all of which need to be run and managed throughout the testing vehicle. This integration is time consuming and problematic for field service.

SUMMARY

The above-identified need is met by the present rail condition monitoring carriage and system, that allows the core technology used in conventional SST testing to be deployed on an independent carriage, which is preferably towed behind a typical railroad hy-rail vehicle. Alternatively, the present carriage is contemplated as being pushed by a rail vehicle, carried underneath the vehicle, being self-propelled or otherwise moved along the rail as needed for monitoring rail condition while moving. Using the present carriage, the rail track inspector performs his customary visual monitoring of the track, while the present rail condition monitoring carriage simultaneously monitors the rail condition in a similar manner as performed by the stop start test systems. As the monitoring carriage travels the rail, sensing data is collected and preferably transmitted to a remote database. This technology differs from conventional stop start test (SST) systems because the present system does not employ real-time display and corresponding interactive decisions of the operator.

Instead, the track inspector primarily monitors an in-vehicle illuminated indicator, such as a red light/green light scenario, wherein the illumination of a particular color indicates at least one of proper operation of the system, acceptable rail condition, the presence of a rail flaw or the like. The indicators may be constantly illuminated or flashing to reflect various monitored conditions. Using the present system, internal rail condition data is collected on the rail as frequently as the track inspector traverses the rail. This approach changes the periodic inspection of the railroad for defects to a proactive monitoring of the health of the rail. Using this collected data, each data collection event is compared with prior data from the same location, and the railroad is provided with alerts as defined by the railroad as to the presence and growth of anomalies.

The present system thus provides the railroad with the capability for converting from reactive to proactive rail condition monitoring, thus, preventing rail failures and lowering rail maintenance costs, in that power sources needed to operate the carriage are provided by the hy-rail vehicle.

The present carriage features a quick release design that enables testing of track with a Look-Out, an individual the railroad assigns to a maintenance crew to watch for trains to properly schedule rail maintenance work. In addition, the present carriage is optionally uncoupled from the Test Vehicle and, with the aid of long cables can be pushed on a given section of track and used as a fully functional walk behind unit. Often Test Vehicles are not allowed on sections of track due to train traffic and this optional walk behind function allows an operator to test that section of track. Alternately, instead of long cables, the carriage is optionally configured to be a stand-alone modular unit configured for sensing and wirelessly transmitting data generated by ultrasonic sensing of the rail. Such wireless communication is achieved by placing a portion of the ultrasonic hardware on the carriage in close operational proximity to the sensor wheel, and the remainder of the hardware on the hy-rail vehicle.

When used as a stand-alone walk behind test system, a wireless handheld device is incorporated into the monitoring process along with a unique wireless communication between the carriage, hand held device and an off site data collection center.

With conventional ultrasonic rail testing devices, the ability to follow the varying gage of the rail or the separation between the rails is needed for accurate testing. The present carriage monitors rail gage or gauge by applying pressure to the carriage wheels against the gage side of the track. In the present carriage, the gage measuring actuators not only perform the gage following as conventional carriages do, but also measure the distance each actuator is extended-retracted. This information is fed to the control system, where it is interpolated into a true gage measurement. Excessive rail gage wear is one way in which a derailment may occur, and the present hitch mount carriage constantly monitors the gauging actuators and alerts the test vehicle crew when appropriate.

In conventional SST test vehicles, there is a need for a crew of up to 4 personnel, an operator's station outfitted with racks of hardware, computer and multiple monitors in order to properly test track. With the present carriage, the required number of operators is reduced to a passenger seat mounted electrical hardware box and a standard laptop computer mounted to a swing arm with a crew of one.

The present carriage also has the capability to perform data collection on any hy-rail equipped vehicle with a driver relatively un-skilled in ultrasonic gage and rail flaw inspection. In the preferred embodiment, the data collected by the carriage is sent to an off-site collection system where it is analyzed by trained rail flaw testers and reported back to the track maintenance group for action when required.

On conventional test carriages, significant downtime occurs when the sensor wheels need to be repaired or exchanged for new or different technology. The removal of the sensor wheel and cable along with the installation and running of the new set is very time consuming. In answer to the industry need to reduce the downtime for repairs and technology changes, the present carriage features a quick-change transducer wheel. A single dovetail bolt and ¼ turn connector are disconnected to remove any sensor wheel. The operator then slides a quick change sensor wheel into the loose dovetail, tightens the single bolt and ¼ turn cable and the software recognizes the newly installed sensor wheel, and the system is ready to test.

On conventional SST test vehicles, the need for constant monitoring of the track web is necessary for an accurate test. This is achieved by a trained rail tester constantly monitoring an oscilloscope for the correct ultrasonic response that indicates true web alignment. In the present hitch test carriage, an optional auto-alignment feature constantly measures the distance from the main "0" degree transducer in the sensor wheel to the center of the rail web and sends feedback to the control unit of the system, which facilitates self adjusting of the sensor wheels to a desired test position. This apparatus provides accurate rail web data without monitoring and without expensive oscilloscope equipment used in conventional SST vehicles.

An ultrasonic track testing system and method for movement along rails in operative relationship with a test vehicle performing ultrasonic flaw inspection is disclosed. The system includes a pair of wheel frames with leading and trailing guide alignment wheels for following the gage side of the rail and ultrasonic sensing mounted in a working relationship with the rail for detecting changes in the rail and the position of the sensing means relative to the rail with a main frame disposed between wheel frames and adapted to be coupled with the hitch mounting of any test vehicle for movement therewith. Interconnecting means extends between the main frame and each of the wheel frames so as to permit each wheel frame independent freedom of motion relative to the main frame in a plane substantially perpendicular to the gage side of the rail while simultaneously maintaining parallelism between the wheel frames. The ultrasonic sensing apparatus associated with each wheel frame is adjustable in a vertical, lateral and angular plane relative to the rail being inspected. In the preferred embodiment, the ultrasonic sensor assembly is prevented from losing contact with the track section being tested by down pressure exerted on the test carriage center frame by a fluid power actuated cylinder.

More specifically, A rail condition monitoring carriage for use on a railroad track is provided, including at least one frame movable along the railroad track, an ultrasonic rail condition monitor disposed on the at least one frame and configured for ultrasonically monitoring condition of the railroad track and transmitting the condition data to a remote location, a gage measurement device disposed on the at least one frame for monitoring a gage value of the track, collecting gage data and transmitting the gage data to the remote location, and a control system connected to the rail condition monitor and the gage measurement device for receiving the collected data and evaluating same.

In another embodiment, a method is provided for measuring rail gage, including, providing an ultrasonic rail condition monitor for ultrasonically monitoring condition of the railroad track and transmitting said condition data to a remote location, a gage measurement device for monitoring a gage value of the track, collecting gage data and transmitting the gage data to the remote location and a control system connected to the rail condition monitor and the gage measurement device for receiving the collected data and evaluating same; and configuring the control system for using the formulae:

$$GX=AX+EX+FX \text{ and } G=G1+G2$$

Wherein:
G=Overall Gage Measurement (inch)
GX=Side Specific Gage measurement (inch)
AX=Distance from Center to Actuator Zero Point (inch)
EX=Actuator extension (inch) and
FX=Distance from Actuator to Rail Face.

In still another embodiment, a rail condition data system is provided, including a unitized mounting substrate, an ultrasonic rail condition monitor disposed on the substrate and configured for ultrasonically monitoring condition of a railroad track and transmitting the condition data to a remote location. A gage measurement device is disposed on the substrate for monitoring a gage value of the track, collecting gage data and transmitting the gage data to the remote location, and a control system is connected to the rail condition monitor and the gage measurement device for receiving the collected data and evaluating same.

DETAILED DESCRIPTION

Figure 1:
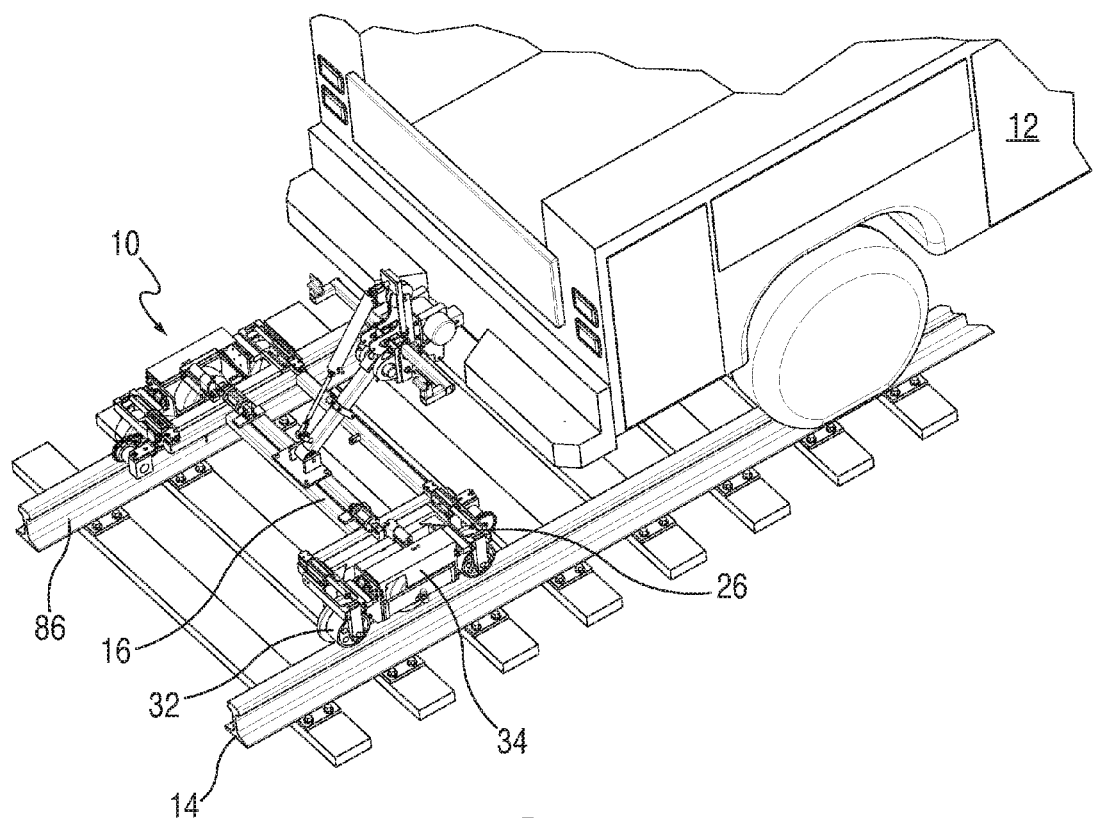
FIG. 1 is a top rear perspective view of the present rail condition monitoring carriage mounted to a conventional hy-rail vehicle for monitoring track condition.

Referring now to FIG. 1, the present rail condition monitoring carriage, generally designated 10, is shown mounted to the rear of a conventional rail maintenance vehicle 12 such as a hy-rail vehicle of the type commonly used on railroads. The vehicle 12 is a standard truck equipped with front and rear rail bogie wheel assemblies (not shown) for use in traveling along railroad track, generally designated 14. A large percentage of rail track inspection is performed visually by operators using vehicles 12. An important feature of the present carriage 10 is that it makes more effective use of the conventional visual inspection process, by enhancing the capabilities of the vehicle 12 and providing more accurate and detailed rail condition data.

Figure 2:
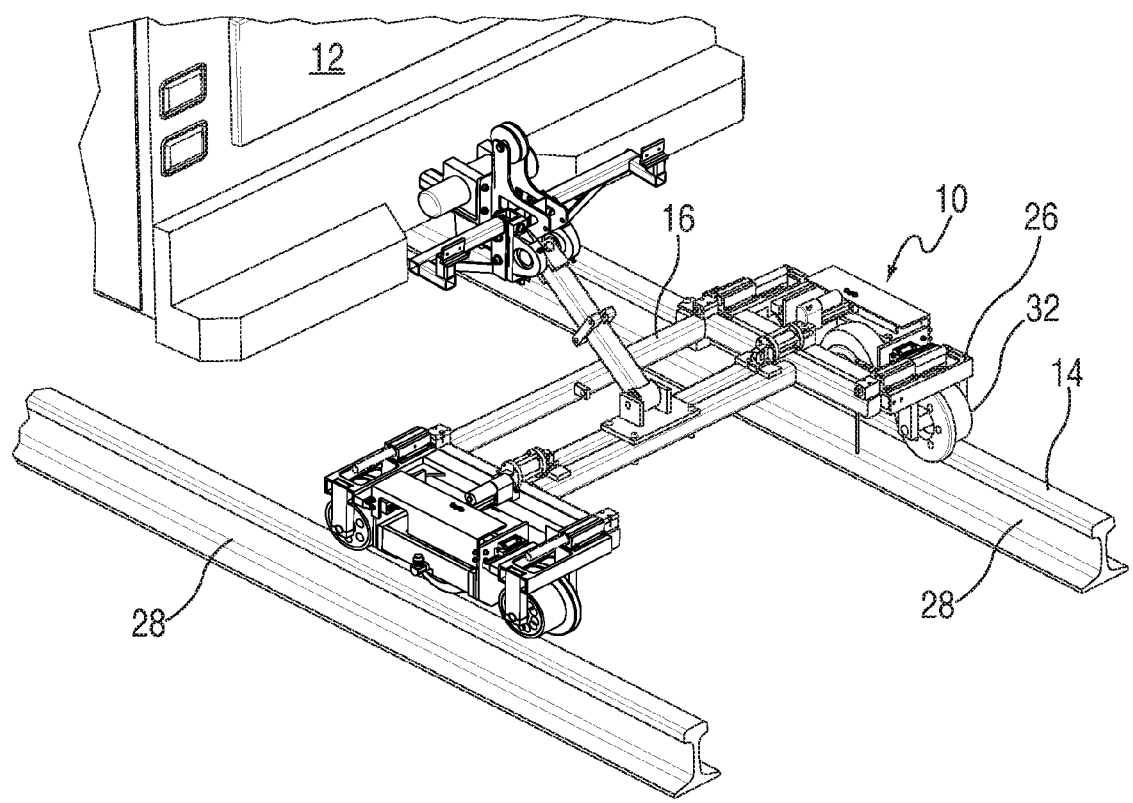
FIG. 2 is an enlarged top perspective view of the present rail condition monitoring carriage as seen in FIG. 1.
Figure 3:
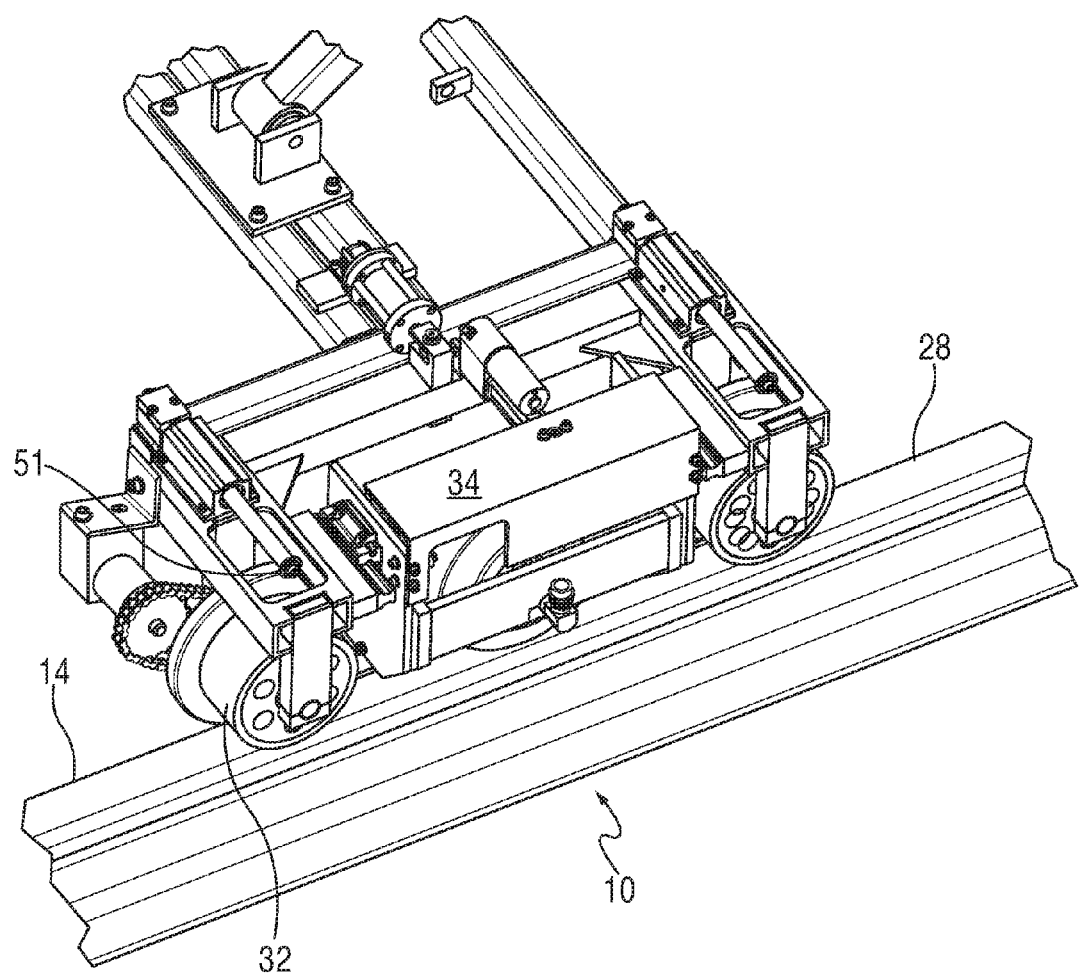
FIG. 3 is a fragmentary enlarged top perspective view of the carriage shown in FIG. 2.
Figure 4:
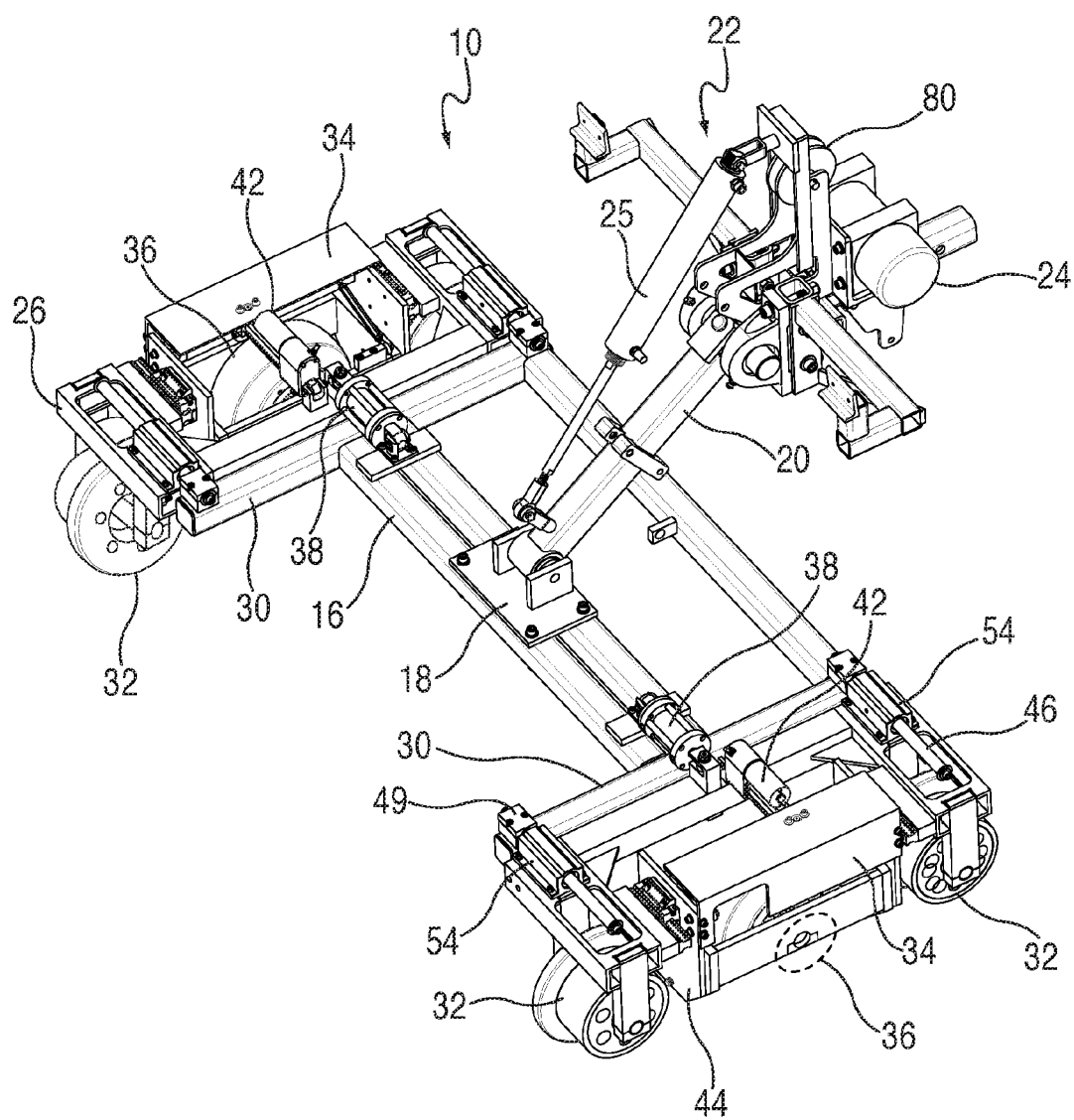
FIG. 4 is an enlarged top perspective view of the present rail condition monitoring carriage.

Referring now to FIGS. 2-4, the carriage 10 includes a central frame 16 preferably having an open, rectangular configuration; however other shapes and arrangements are contemplated. A clevis mount 18 on the central frame 16 provides a pivot mount for an elongate lift arm 20 connected at an opposite end to a hitch bracket, generally designated 22. The hitch bracket 22 is configured for being secured to the conventional hitch (not shown) that is standard equipment for hy-rail vehicles 12. Also included on the hitch bracket 22 is a winch or other similar type of extending or retracting mechanism 24 used for raising and lowering the carriage 10 relative to the track 14 between a working and a travel position, as is well known in the rail maintenance art. A mechanical actuator, such as a pressurized fluid power cylinder 25 or the like is mounted on the lift arm 20 at one end and the hitch bracket 22 at the other for exerting a downward force on the carriage 10 when the carriage is in the working position and preventing it from lifting up during turbulent travel.

Also included on the carriage 10 is a combined gage tracking and Rolling Search Unit wing or subframe, generally designated 26, one such subframe associated with each of the rails 28 of the track 14. While various shapes are contemplated, in the preferred embodiment, the subframe 26 has a generally "["-shape when viewed from above. As will be described in further detail below, each subframe 26 is laterally movable relative to the central frame 16, and preferably relative to side brackets 30 of the central frame, to adjust the gage of the carriage and provide gage readings of the track 14. In the preferred embodiment, the side brackets 30 extend linearly along an axis parallel to the rails 28. Rail gage variations are an important indicator of rail condition.

At least one and preferably a pair of flanged, gage tracking or carriage wheels 32 are associated with, and move as a unit with each associated subframe 26, and are contact points between the carriage 10 and the track 14. In addition, a Rolling Search Unit 34 located between the tracking wheels 32 includes an ultrasonic sensing wheel 36 configured for ultrasonically checking the associated rail 28 for flaws.

An actuator 38, preferably a pneumatic actuator, is associated with each subframe 26 and is controlled by a central control system 40 (FIG. 15) for exerting gage out pressure against the subframe and sensing variations in the lateral displacement of the subframes relative to the central frame 16, thus measuring gage, since the actuators are configured for transmitting sensed lateral displacement variations to the control system 40. In addition, a preferably electric actuator 42 similarly adjusts the lateral position of an RSU positioning frame 44 and particularly the ultrasonic sensing wheel 36 relative to the central frame 16.

Figure 5:
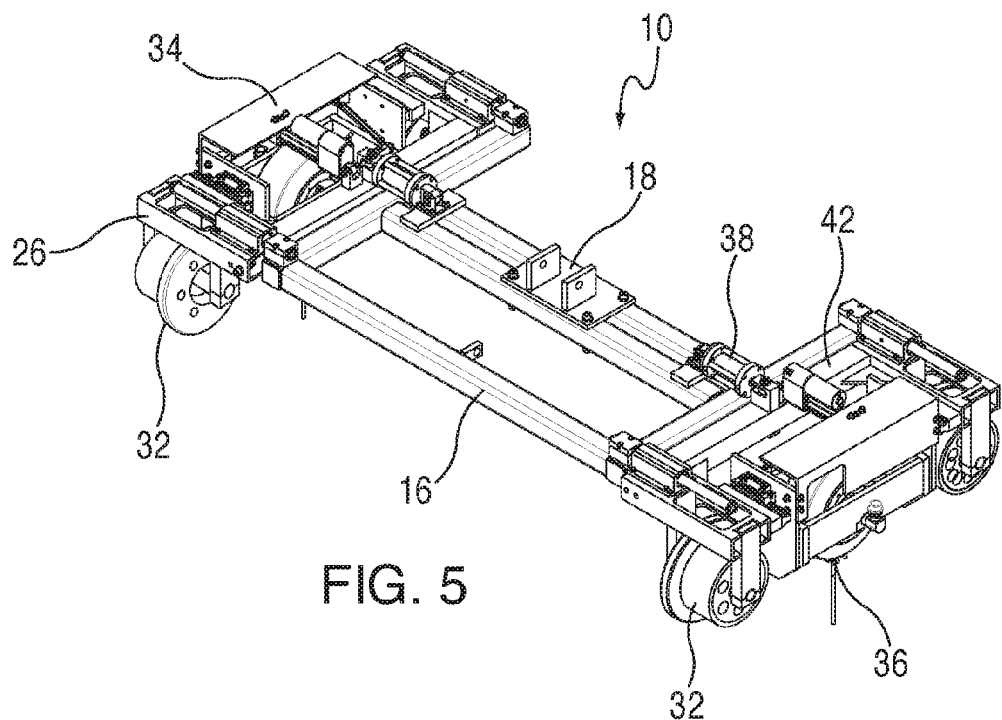
FIG. 5 is a fragmentary top perspective view of the assembled present carriage without the hitch assembly.
Figure 6:
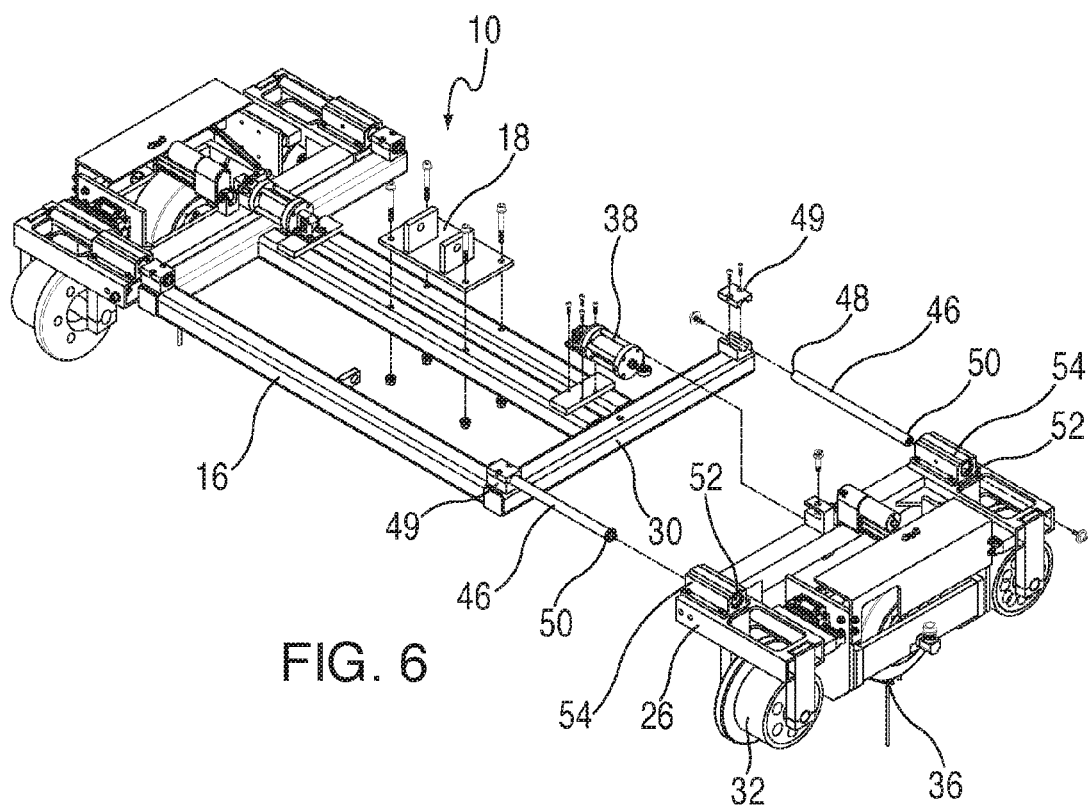
FIG. 6 is a partially exploded top perspective view of the structure of FIG. 5.

Referring now to FIGS. 5 and 6, the subframes 26 are virtually identical, and as such, only one will be described in detail. As discussed above, the subframes 26 reciprocate laterally relative to the central frame 16. To maintain a desired alignment between the subframe 26 and the central frame 16, a guide apparatus in provided, including gage shafts 46 fixed at a first end 48 to the side bracket 30 of the central frame 16 by a clamp 49, the opposite end 50 being free. The gage shafts 46 slidingly and matingly engage throughbores 52 in guide brackets 54 located at each front and rear end of the subframe 26, in locations associated with the gage tracking wheels 32. Thus, as the actuator 38 urges the subframe 26 away from the central frame 16, the subframe slides along the gage shafts 46 to maintain alignment. The free ends 50 are provided with large diameter washers 51 (FIG. 3) for preventing the brackets 54 from becoming disengaged from the shafts 46.

While the central frame 16 and relatively movable gage subframes 26 are disclosed here, variations of the structure are contemplated, including two subframes connected to each other so as to be relatively movable there to for adjusting to rail gage, or alternately, a central or main frame having the gage tracking wheels and/or the RSU unit 34 mounted thereto for relative movement so that desired rail condition and rail gage data is collected.

Figure 7:
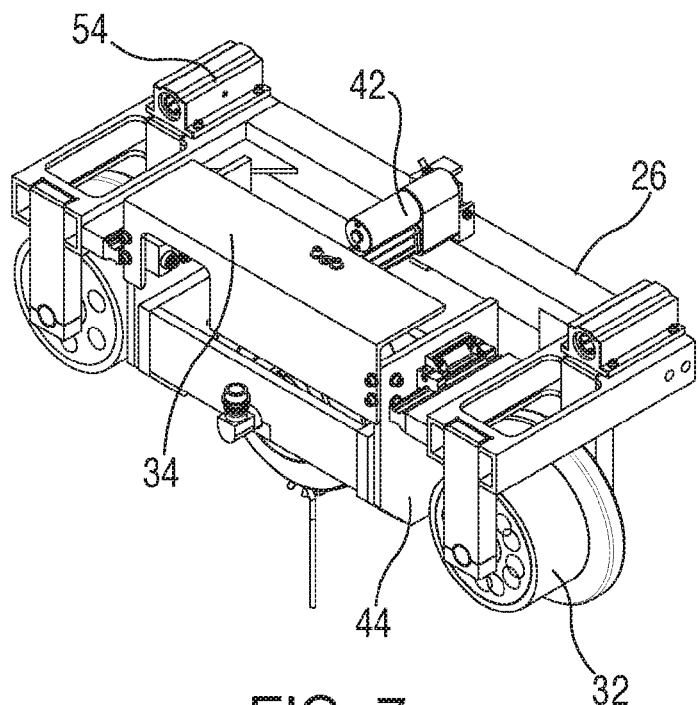
FIG. 7 is a top perspective assembled view of the present gage tracking and Rolling Search Unit assembly.
Figure 8:
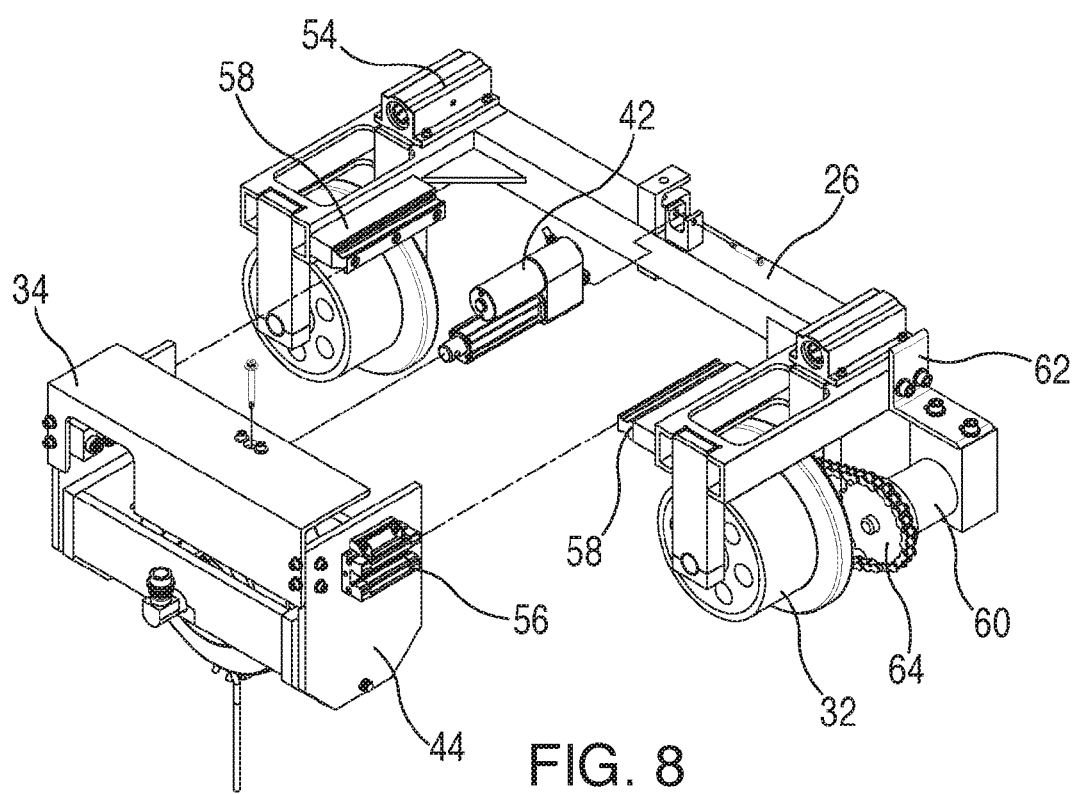
FIG. 8 is an exploded perspective view of the structure of FIG. 7.

Referring now to FIGS. 7 and 8, the RSU unit 34 is depicted in greater detail. The RSU positioning frame 44 is laterally slidable relative to the subframe through engagement between guide brackets 56 on the frame that define a dove-tail-type track, and slidingly and matingly engage corresponding guide bars 58 mounted to the subframe 26 in a horizontal orientation. Lateral reciprocating movement by the electric actuator 42 displaces the RSU positioning frame 44 laterally relative to the subframe 26 and to the rail 28 along the brackets 56, and sends position feedback data to the control system 40.

At one end of the subframe 26, an encoder 60 is mounted, as by an encoder bracket 62 to be in operational proximity to a designated gage tracking wheel 32 for determining track position of the carriage 10. Through a drive mechanism 64, preferably a chain, belt, or direct drive, movement of the tracking wheel 32 drives the encoder 60, and generates distance traveled data, which is also transmitted to the control system 40.

Figure 9:
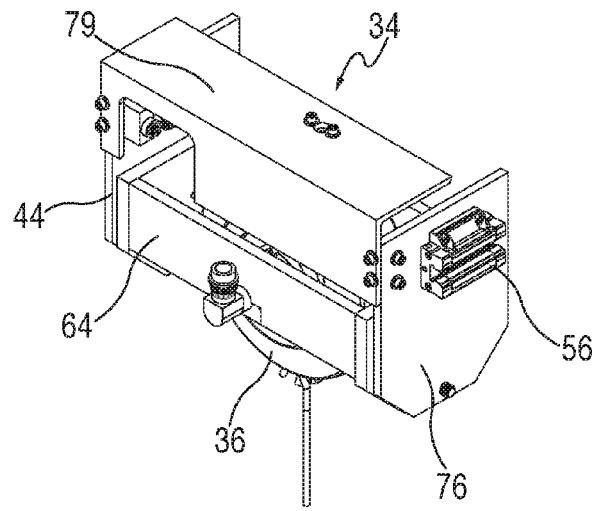
FIG. 9 is a top perspective, assembled view of the Rolling Search Unit assembly.
Figure 10:
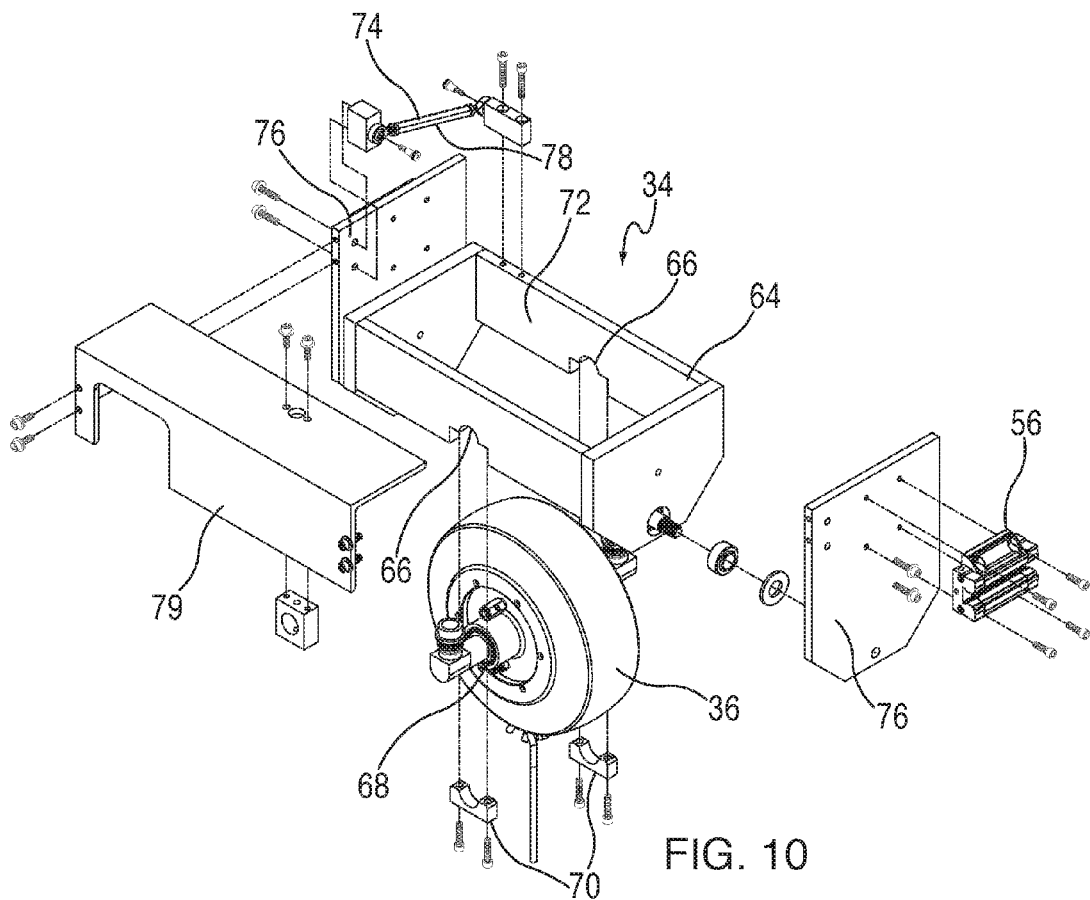
FIG. 10 is an exploded perspective view of the structure of FIG. 9.

Referring now to FIGS. 9 and 10, a central component of the RSU unit 34 is the ultrasonic sensing wheel 36, which in operation is disposed to roll upon a top surface of the rail 28. As is known in the art, the wheel 36 is provided with embedded ultrasonic sensors (not shown), which detect flaws in the rail 28. A mount box 64 includes a pair of opposed axle recesses 66 for receiving an axle 68 of the sensing wheel 36. Axle clamps 70 retain the axle 68 in the axle recesses. In addition, the mount box 64 defines an inner chamber 72 dimensioned for accommodating the sensing wheel 36. Angular adjustment of the position of the RSU unit 34 upon the rail 28 is achieved with an actuator 38 as described above, or a turnbuckle assembly 74 having one end mounted to a pivoting endplate 76, and the opposite end being attached to the mount box 64. Since the endplate 76 is the base for the guide tracks 56, axial adjustment of a length of a turnbuckle rod 78 causes pivoting of the mount box 64 about a longitudinal mount box axis, thus changing the angular orientation of the sensing wheel 36 relative to the rail 28. It will be appreciated that the mount box 64 pivots relative to both endplates 76. Also, a support bracket 79 is joined to each of the end plates 76 for increased rigidity.

Figure 11:
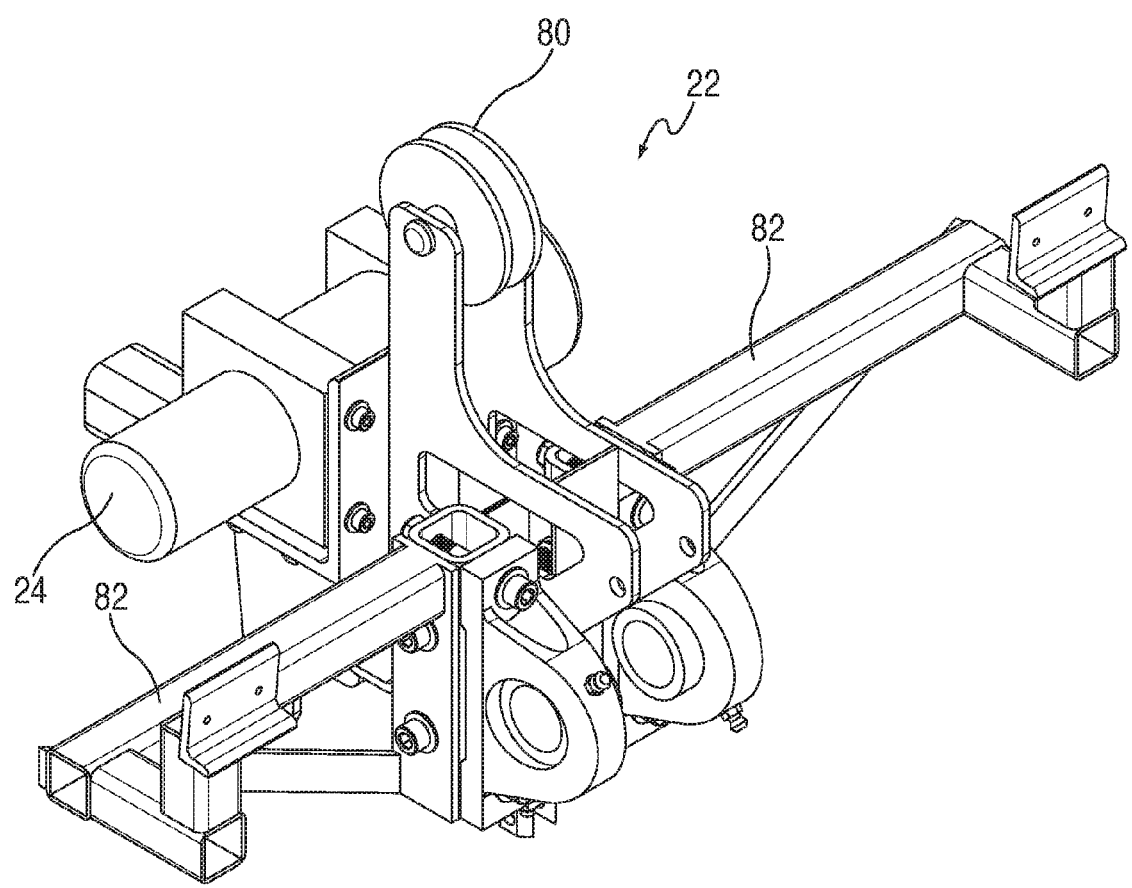
FIG. 11 is a top perspective view of the present hitch mount bracket.

Referring now to FIG. 11, the hitch bracket 22 includes a pulley 80 for supporting a cable of the winch 24 that is used to move the carriage 10 from the working to the travel positions. Carriage support arms 82 extend laterally from a central bracket portion 84 and provide support for the carriage 10 when in the travel position.

Figure 12:
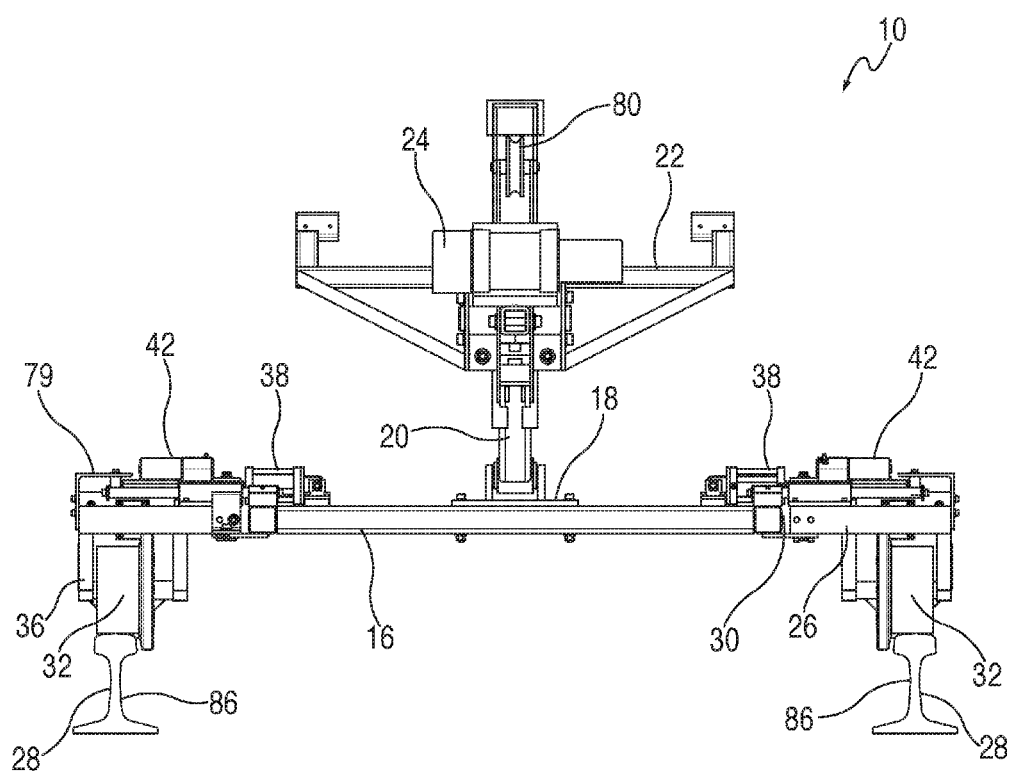
FIG. 12 is a rear elevation of the present rail condition monitoring carriage.

Referring now to FIG. 12, with conventional ultrasonic testing units, the ability to follow the varying gage of the rail 28 is needed for obtaining accurate testing. The actuators 38 on the central frame 16 exert a laterally outwardly directed pressure against the gage tracking wheels 32. In the present carriage, the actuators 38 not only perform gage following, they also measure the distance each actuator is extended-retracted and feeds this information to the control system 30 where it is interpolated into a true gage measurement.

Excessive rail gage wear is a common cause for derailment, and the present hitch mount carriage constantly monitors the actuators 38 and alerts the test vehicle crew when gage data exceeds acceptable distances.

More specifically, the data supplied by the actuators 38 is analyzed using the following formulae:

$$G_x = A_x + E_x + F_x$$

$$G = G_1 + G_2$$

Wherein:
G=Overall Gage Measurement (inch)
GX=Side Specific Gage measurement (inch)
AX=Distance from Center to Actuator Zero Point (inch)
EX=Actuator extension (inch)
FX=Distance from Actuator to Rail Face [gage side surface of rail head] (inch)
$G_1$ and $G_2$ are sequential gage measurements by the present carriage 10. The resulting value when compared to the theoretical value will determine whether the track is under/over gage. If the calculated gage value is either over or under preset acceptable ranges, the control system 40 alerts the operator so that the rail can be repaired.

Figure 13:
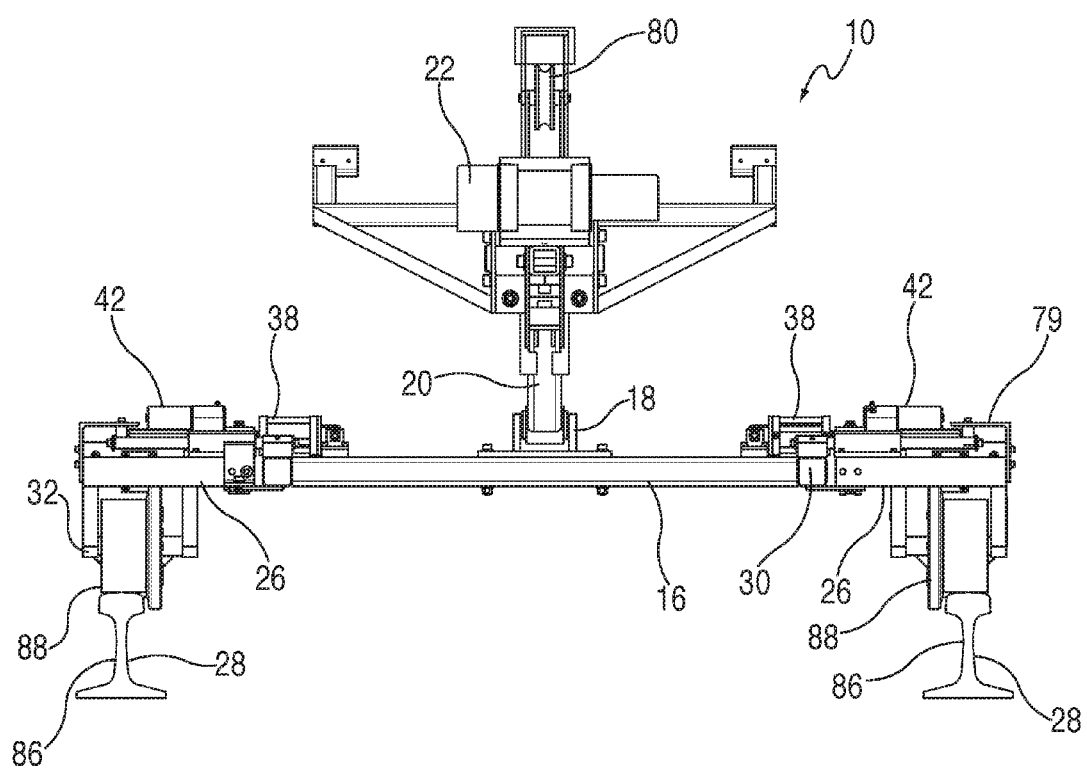
FIG. 13 is a rear elevation of an alternate embodiment of the carriage depicted in FIG. 12.

Referring now to FIG. 13, on conventional test vehicles, there is constant ultrasonic monitoring of the rail web 86 to determine whether flaws in the rail are present, and also to ensure that the web is in proper alignment. Conventionally, a trained rail test operator constantly monitors an oscilloscope for the correct ultrasonic response that indicates true web alignment. In the present carriage 10, an alignment feature constantly measures the distance from a main "0" degree transducer in the sensor wheel 36 to the center of the web 86. Measurement is accomplished using lasers 88 located on the subframes 26. This insures an accurate test without monitoring and without the expensive oscilloscope equipment. The web alignment is performed according to the following formulae:

$$L_x = M_x \times \cos \alpha$$

$$W_x = L_x - G$$

Wherein:
$M_x$=Measured distance from Laser to Opposite Web
a=Angle of laser (degrees)
$W_x$=Distance from Gage face to Web (inch)
$L_x$=Distance to Web from Opposite Gage Face (inch)

The resulting value $W_x$, when compared to the preset theoretical value in the control system 40, will determine how much in either direction the lateral actuator needs to move. The present use of lasers 88 has proved beneficial, because it has been found that while the pneumatic actuators 38 measure the distance between gage faces of the rail 28, this data is only for gross positioning of rail wheels on the rail, not the actual center-to-center distance of the rail. As the rail 28 is used, the gage face tends to wear, slowly eroding away the metal on the gage side of the rail head. As such, while the gage tracking wheels 32 will maintain contact and measure the gage, the entire subframe 26 has subsequently moved further out from the center of the track 14 and thusly the centerline of the rail. When this occurs, the RSU 34 is no longer properly positioned relative to the centerline of the rail, requiring lateral adjustment inward relative to the subframe 26. Additionally, a typical fix for gage wear is to simply flip the rail 28 around, making the old field side of the rail head the new gage side of the rail head. When this (or a similar rail condition) happens, the subframe 26 can be pushed further toward the center of the track, and subsequently the RSU 34 is moved further inward from the centerline of the rail, requiring lateral adjustment outward to put it back in alignment. The lasers 88 provide more accurate readings.

Accordingly, the control system 40 is configured for aligning the ultrasonic rail condition monitor automatically. The web alignment system described above generates a feedback loop whereby the ultrasonic sensing RSU unit 34 is automatically adjusted for obtaining the strongest signal.

Referring to FIGS. 9, 10, 12 and 13, another feature of the present carriage 10 is that once an operator performs an initial equipment set-up procedure, and the rail condition and gage data collection commences, the control system 40 is configured so that the ultrasonic sensing wheel 36 or equivalent device is automatically aligned to the rails 28 without the need for continuous operator observation, interpretation or interaction.

Figure 14:
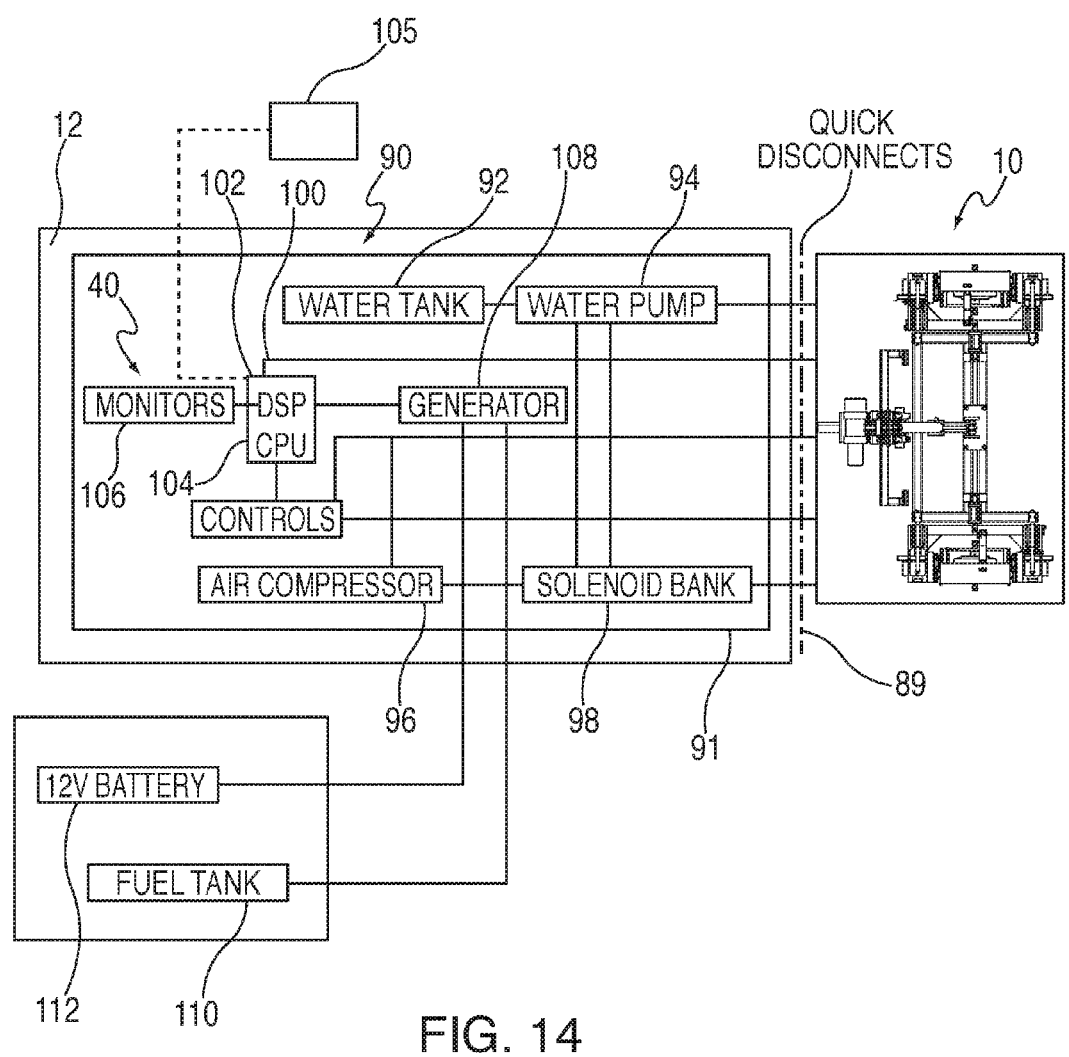
FIG. 14 is a schematic depicting the connections for the various operational utilities used by the present rail condition monitoring vehicle.

Referring now to FIG. 14, another feature of the present carriage 10 is that there are several resource connections that are relatively easily made between the carriage and the hy-rail vehicle 12. These connections, shown schematically at 89 in FIG. 14, are converted to quick connections between the carriage 10 and a modular, preferably palletized Carriage Support Unit (CSU) 90 mounted as a unitized mounting substrate 91, such as on a pallet, the main frame 16 or the like, to the vehicle 12 so that the use of the hy-rail vehicle and the carriage 10 become a rail condition data generator, instead of the more expensive and labor-intensive dedicated SST vehicle. It is also contemplated that the unit 90 is operable independently of the vehicle 12 for monitoring rail condition and transmitting the data collected through the monitoring process.

Figure 15:
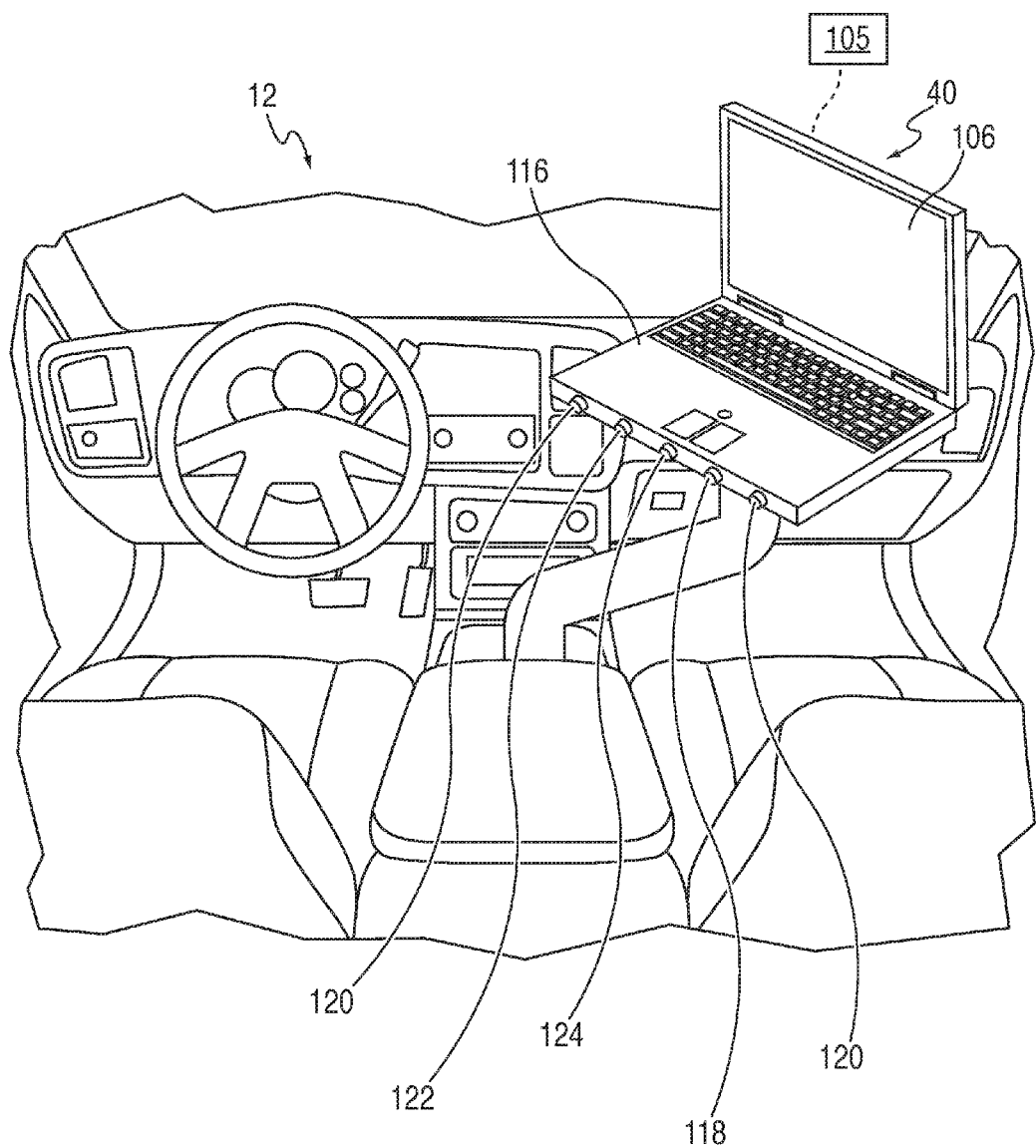
FIG. 15 is a perspective view of the present control system mounted in the cab of a conventional hy-rail vehicle.

Since the RSU 34 requires water as a coupling for proper ultrasonic readings, between the wheel 36 and the rail 28, the CSU 90 is provided with a water tank 92 and a preferably electric water pump 94 connected to the tank for providing water to the sensor wheel 36. Next, a supply of pressurized air for powering the preferably pneumatic actuators 38 and the down cylinder 25 is provided by a preferably 12V air compressor 96 that provides pressurized air to a 12V pneumatic solenoid valve bank 98. The valve bank 98 provides regulated pressurized air to cylinders in the actuators 38, and the cylinder 25 upon receipt of input from the operator via the control system 40. Ultrasonic cables 100 connect the RSUs 34 to a digital signal processing (DSP) system 102, a component of the control system 40. The DSP 102 pulses, receives, and interprets the ultrasonic data from the RSUs 34, transmitting data back and forth with a central processing unit 104, also part of the control system 40. Both the DSP 102 and the CPU 104 also communicate with the controls (FIG. 15) for the carriage 10. This data is processed through software and displayed on at least one monitor 106 preferably located in the operator's cab in the hy-rail vehicle 12 (FIG. 15). Alternately, it is contemplated that at least one of the DSP 102, the CPU 104 and/or the at least one monitor 106 are optionally mounted on the carriage 10. It is also contemplated that the CPU 104 has a preferably remotely located data evaluator component 105 that receives data collected by the various sensing devices on the carriage 10 and transmitted by the control system 40 or the like. The CPU data evaluator component 105 then compares more recently obtained rail condition data and/or gage data with previously obtained data from the same section of rail and compares the relative values for detecting changes in rail condition. In the event discrepancies in the data are determined that are considered significant, as when compared against preset lookup tables, alarm signals in the form of visual, audible, text messages or the like are sent to the railroad or the party in control of the track being tested, so that necessary repairs can be coordinated.

An optional scenario for enhancing wireless communication between the sensor wheel 36 and the control system 40 is to place a portion of the hardware making up the DSP 102 ultrasonic hardware on the carriage in close operational proximity to the sensor wheel, and the remainder of the hardware on the hy-rail vehicle 12. Preferably, the DSP 102 remains on the hy-rail vehicle 12, and a pulser/receiver (not shown) is placed in close operational proximity to the sensor wheel 36 for enhanced signal transmission quality and/or capability.

In addition, a generator 108 or alternate power source, such as an inverter, provides AC power to the DSP 102, CPU 104, the at least one monitor 106, and other auxiliary components. Based on the application, the generator 108 is optionally provided with an external fuel source 110 or battery source 112 (for start-up). The generator 108 is controlled via a factory supplied remote panel (not shown).

Referring now to FIG. 15, the trained operator uses a set of operational switches to control functions on the carriage 10 while seated in the driver's seat 114 of the vehicle 12. The monitor 106, preferably connected to a laptop computer or the like 116, which optionally includes the control system 40, the CPU 104 and the DSP 102, depending on the application. Controls associated with the computer 116 include lateral adjustment of the electronic actuators 42 at 118 for adjusting the RSU 34, engaging of the pneumatic actuators 38 at 120 for providing pressure against each of the rails 28, and for optionally locking these cylinders at their current extension. The latter feature is helpful when traversing certain track geometries. A control for engaging test water flow is shown at 122, and wheel lube control at 124 wets the hy-rail gear on the vehicle 12 to reduce wheel squeal. Other controls are contemplated depending on the situation, and it is also contemplated that in some embodiments, the controls such as those identified as 118-122 are optionally embedded in the software of the control system 40, or a touch screen is optionally provided on the monitor 106.

In addition, the DSP 102 and the CPU 104 are optionally outfitted with a wireless communication hub that enables the use of Run-On-Run software which allows users to see the playback file of a previous run while testing the same area. The Run-On-Run system is disclosed in co-pending, commonly assigned U.S. patent application Ser. No. 13/409,487 filed Mar. 1, 2012, which is incorporated by reference. This also allows for uploading of test data to an off-site facility for review.

Figure 16:
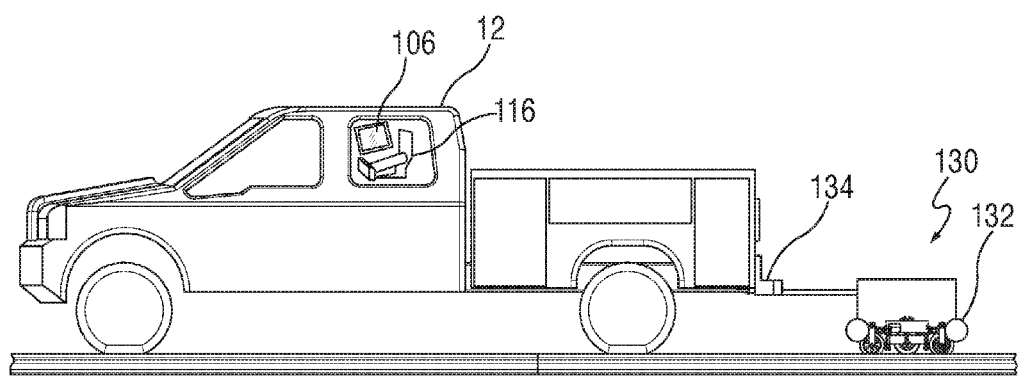
FIG. 16 is a side elevation of another embodiment of the present rail monitoring carriage.

Referring now to FIG. 16, an alternate embodiment of the present carriage 10 is generally designated 130. The carriage 130 differs from the carriage 10 in that the components of the CSU 90 are integrally incorporated into the carriage 130, instead of being located on the hy-rail vehicle 12. As such, the carriage 130 is an independent tow-along package. The carriage, generator, water, pneumatics, DSP, CPU, fuel, and power are packaged together as a unit that can be towed behind any vehicle. The carriage 130 has road wheels 132 for travel that lift out of the way when the carriage is lowered on to the rail. As the system employs several features for automatic alignment and tracking, only a single display cable is needed between the remote monitor station 116 and the carriage 130, since operator input is not required. This allows any hy-rail vehicle that is not specifically intended for rail flaw detection to collect rail defect data. The carriage 130 preferably utilizes a receiver 134 or other known hitch configuration, including but not limited to a ball hitch mount, so it can be quickly swapped between vehicles for testing or travel without required special hardware or equipment. It is also contemplated that the carriages 10, 130 are self-propelled.

While a particular embodiment of the present rail condition monitoring system with carriage has been described herein, it will be appreciated by those skilled in the art that changes and modifications may be made thereto without departing from the invention in its broader aspects and as set forth in the following claims.

What is claimed:

1. A rail condition monitoring carriage for use on a railroad track, comprising:
    at least one frame movable along the railroad track;
    an ultrasonic rail condition monitor disposed on said at least one frame and configured for ultrasonically monitoring condition of the railroad track and transmitting said condition data to a remote location;
    said ultrasonic rail condition monitor including an ultrasonic sensing wheel constructed and arranged for rolling upon a top surface of a rail of the railroad track;
    a gage measurement device disposed on said at least one frame for monitoring a gage value of the track, collecting gage data and transmitting the gage data to the remote location;
    said gage measurement device including at least one horizontal actuator on said at least one frame and associated with a laterally displaceable sub-frame carrying said ultrasonic sensing wheel, said at least one horizontal actuator configured for exerting a gage out pressure on said laterally displaceable sub-frame;
    and a control system connected to said rail condition monitor and said gage measurement device for receiving the collected data and evaluating same.

2. The carriage of claim 1, further including a data evaluator component of said control system configured for receiving said rail condition data and said gage data and comparing relatively recent condition and/or gage data with previously collected and stored condition and/or gage data for detecting changes in the collected data.

3. The carriage of claim 1 wherein said control system is configured for aligning said ultrasonic rail condition monitor automatically.

4. The carriage of claim 2 wherein said data evaluator is configured for transmitting alarm signals in the event said compared data is determined to indicate that rail maintenance is needed.

5. The carriage of claim 1 including said at least one frame and said at least one laterally displaceable sub-frame being configured for movement together along the railroad track.

6. The carriage of claim 1, being configured for being towable by a conventional hy-rail vehicle.

7. The carriage of claim 1, having onboard power, fuel and water supplies and configured to be towed as a complete unit by a conventional hy-rail vehicle.

8. The carriage of claim 1 wherein said ultrasonic monitor is prevented from losing contact with the track section being tested by down pressure exerted on said at least one frame by a generally vertical fluid power actuated cylinder.

9. A rail condition data system, comprising:
A rail condition data system, comprising:
a unitized mounting substrate;
an ultrasonic rail condition monitor disposed on said substrate and configured for ultrasonically monitoring condition of a railroad track and transmitting said condition data to a remote location;
said ultrasonic rail condition monitor including an ultrasonic sensing wheel constructed and arranged for rolling upon a top surface of a rail of the railroad track;
a gage measurement device disposed on said at least one frame for monitoring a gage value of the track, collecting gage data and transmitting the gage data to the remote location;
said gage measurement device including at least one horizontal actuator on said mounting substrate and associated with a laterally displaceable sub-frame carrying said ultrasonic sensing wheel, said at least one horizontal actuator configured for exerting a gage out pressure on said laterally displaceable sub-frame; and
a control system connected to said rail condition monitor and said gage measurement device for receiving the collected data and evaluating same.

10. The system of claim 9, further including:
a water tank disposed on said mounting substrate;
a water pump connected to said tank and to said mounting substrate; and
an air compressor disposed on said mounting substrate.

11. The system of claim 9 wherein said mounting substrate is a frame movable upon the railroad track and is hitch mountable.

12. The system of claim 9 wherein said control system is configured for comparing data transmitted from said monitor and said device and comparing said data with pre stored data to determine if rail maintenance is required.

13. The system of claim 9 wherein said mounting substrate is selectively connectable to a rail maintenance vehicle and independently operable relative to the rail maintenance vehicle.

* * * * *